(12) United States Patent
Liverton et al.

(10) Patent No.: US 6,403,596 B1
(45) Date of Patent: Jun. 11, 2002

(54) SUBSTITUTED PYRIDONES HAVING CYTOKINE INHIBITORY ACTIVITY

(75) Inventors: Nigel J. Liverton, Harleysville; David A. Claremon, Maple Glen; John W. Butcher, Telford, all of PA (US); Cory R. Theberge, Portsmouth, NH (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/592,029

(22) Filed: Jun. 12, 2000

Related U.S. Application Data

(60) Provisional application No. 60/141,333, filed on Jun. 28, 1999.

(51) Int. Cl.[7] .................... C07D 401/04; A61K 31/506; A61P 19/10
(52) U.S. Cl. ................. 514/256; 514/275; 544/331; 544/333
(58) Field of Search .................. 544/331, 333; 546/257; 514/275, 256, 334

(56) References Cited

FOREIGN PATENT DOCUMENTS

| EP | 308020 A2 | * | 3/1989 |
| EP | 0308 020 | | 3/1989 |
| JP | 60-94964 A | * | 5/1985 |
| WO | WO 98/24780 | | 6/1998 |

OTHER PUBLICATIONS

Chemical Abstract, vol. 104(1):5780e (1985).
Chemical Abstract, vol. 117(17):171167y (1992).
Chemical Abstract, vol. 114(5):42638s (1991).
Chemical Abstract, vol. 72(11):55331a (1970).
CAPLUS electronic database printout 1986:5780, JP60094964.
CAPLUS electronic database printout 1992:571167, A Krauze, et al. Khim. Geterotsiki. Soedin, vol. 12, pp. 1674–1679 (1991).
CAPLUS electronic database printout 1991:042638, M.M. El–Kerdawy, et al., Orient. J. Chem., vol. 6, pp. 115–119 (1990).
CAPLUS electronic database printout 1990:55331, F. Kroehnke, et al., Chem. Ber., vol. 103, pp. 322–324 (1970).
Poli, G., et al., Proc. Natl. Acad. Sci. USA, vol. 87, pp. 782–785, 1990.
Dinarello, C.A., Reviews of Infectious Diseases, vol. 6(1), pp. 51–95, 1984.

* cited by examiner

Primary Examiner—Mukund J. Shah
Assistant Examiner—Thomas C. McKenzie
(74) Attorney, Agent, or Firm—Shu M. Lee; David L. Rose

(57) ABSTRACT

There are disclosed compounds of formula (I)

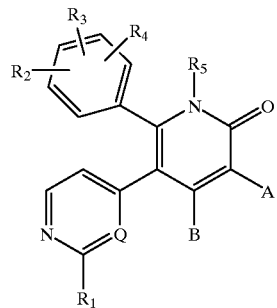

and pharmaceutically acceptable salts thereof which exhibit utility for the treatment of cytokine mediated diseases such as arthritis.

4 Claims, No Drawings

SUBSTITUTED PYRIDONES HAVING CYTOKINE INHIBITORY ACTIVITY

This application claims the benefit of U.S. Patent Application No. 60/141,333, filed Jun. 28, 1999.

BACKGROUND OF THE INVENTION

The present invention relates to substituted heterocyclic compounds which have cytokine inhibitory activity. Cytokine mediated diseases and cytokine inhibition, suppression and antagonism are used in the context of diseases or conditions in which excessive or unregulated production or activity of one or more cytokines occurs. Examples of cytokines which are effected typically include Interleukin-1 (IL-1), Interleukin-6 (IL-6), Interleukin-8 (IL-8) and Tumor Necrosis Factor (TNF).

Interleukin-1 (IL-1) and Tumor Necrosis Factor (TNF) are produced by a variety of cells which are involved in immunoregulation and other physiological conditions.

There are many disease states in which IL-1 is implicated. Examples are rheumatoid arthritis, osteoarthritis, endotoxemia, toxic shock syndrome, acute and chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes.

Interleukin-1 has been demonstrated to mediate a variety of biological activities thought to be important in immunoregulation and other physiological conditions. Dinarello et al., *Rev. Infect. Disease*, 6, 51 (1984). The known biological activities of IL-1 include the activation of T helper cells, induction of fever, stimulation of prostaglandin or collagenase production, neutrophil chemotaxis, induction of acute phase proteins and the suppression of plasma iron levels.

Excessive or unregulated tumor necrosis factor (TNF) production or activity has been implicated in mediating or exacerbating rheumatoid arthritis, rheumatoid spondylitis, osteoarthritis, gouty arthritis, and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejections, fever and myalgia due to infection, cachexia secondary to infection or malignancy, cachexia secondary to acquired immune deficiency syndrome (ADS), AIDS related complex (ARC), keloid formation, scar tissue formation, Crohn's disease, ulcerative colitis and pyresis.

Monokines, such as TNF, have also been shown to activate HIV replication in monocytes and/or macrophages [See Poli, et al., *Proc. Natl. Acad. Sci.*, 87:782–784 (1990)], therefore, inhibition of monokine production or activity aids in limiting HIV progression. TNF has been implicated in various roles with other viral infections, such as the cytomegalovirus (CMV), influenza virus and the herpes virus.

Interleukin-6 (IL-6) is a cytokine effecting the immune system and hematopoiesis. It is produced by several mammalian cell types in response to agents such as IL-1, and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, endothelial cells and ketainocytes. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD 11b/CD 18) on neutrophils without de novo protein synthesis.

There remains a need for compounds which are useful in treating cytokine mediated diseases, and as such, inhibit, suppress or antagonize the production or activity of cytokines such as IL-1, IL-6, IL-8 and TNF.

SUMMARY OF THE INVENTION

The present invention relates to compound I of the formula:

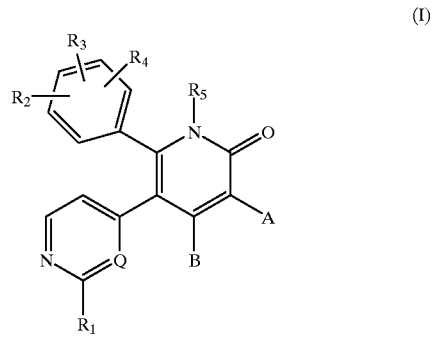

(I)

wherein:

A is hydrogen, CN, COOH, $NO_2$, COO($C_1$–$C_6$ alkyl), ($C_1$–$C_6$ alkyl)-$NH_2$, $CONR_6R_7$;

B is hydrogen or $C_1$–$C_6$ alkyl;

Q is CH or N;

$R_1$ is hydrogen, NH($C_0$–$C_6$ alkyl) aryl or NH($C_1$–$C_6$ alkyl)-O—($C_1$–$C_6$ alkyl);

$R_2$, $R_3$ and $R_4$ independently represent a member selected from the group consisting of hydrogen, halogen, hydroxy, $CF_3$, $NH_2$, $NO_2$, $C_1$–$C_6$ alkyl, $C_1$–$C_6$ alkoxy, $C_3$–$C_8$ cycloalkyl or aryl;

$R_5$ is hydrogen or $C_1$–$C_6$ alkyl;

$R_6$ and $R_7$ are independently hydrogen, $C_1$–$C_6$ alkyl or a saturated 4 to 10 membered mono or bicyclic heterocyclic ring containing at least one N atom, and optionally containing 1–2 additional N atoms and 0–1 S or O atom; or $R_6$ and $R_7$ are taken together with the nitrogen atom to form a saturated 5 to 7 membered heterocyclic ring containing at least one N atom, and optionally containing 1–2 additional N atoms and 0–1 S or O atom, said ring optionally substituted by 1–3 groups selected from $C_1$–$C_6$ alkyl, halogen, hydroxy, $CF_3$, $NH_2$ and $NO_2$;

or a pharmaceutically acceptable addition salt and/or hydrate thereof, or where applicable, a geometric or optical isomer or racemic mixture thereof.

This invention also relates to a pharmaceutical composition which is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective for treating said cytokine mediated disease.

DETAILED DESCRIPTION OF THE INVENTION

The present invention relates to compound I of the formula

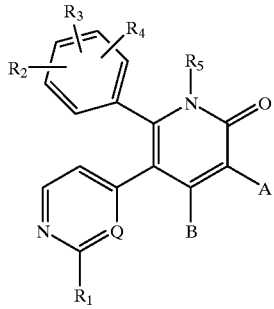

wherein:
A is hydrogen, CN, COOH, $NO_2$, COO($C_1$–$C_6$ alkyl), ($C_1$–$C_6$ alkyl)-$NH_2$, $CONR_6R_7$;
B is hydrogen or $C_1$–$C_6$ alkyl;
Q is CH or N;
$R_1$ is hydrogen, NH($C_{0-6}$ alkyl) aryl or NH($C_1$–$C_6$ alkyl)-O—($C_1$–$C_6$ alkyl);
$R_2$, $R_3$ and $R_4$ independently represent a member selected from the group consisting of hydrogen, halogen, hydroxy, $CF_3$, $NH_2$, $NO_2$, $C_1$–$C_6$ alkyl, $C_1$–$C_6$ alkoxy, $C_3$–$C_8$ cycloalkyl or aryl;
$R_5$ is hydrogen or $C_1$–$C_6$ alkyl;
$R_6$ and $R_7$ are independently hydrogen, $C_1$–$C_6$ alkyl or a saturated 4 to 10 membered mono or bicyclic heterocyclic ring containing at least one N atom, and optionally containing 1–2 additional N atoms and 0–1 S or O atom; or
$R_6$ and $R_7$ are taken together with the nitrogen atom to form a saturated 5 to 7 membered heterocyclic ring containing at least one N atom, and optionally containing 1–2 additional N atoms and 0–1 S or O atom, said ring optionally substituted by 1–3 groups selected from $C_1$–$C_6$ alkyl, halogen, hydroxy, $CF_3$, $NH_2$ and $NO_2$;
or a pharmaceutically acceptable addition salt and/or hydrate thereof, or where applicable, a geometric or optical isomer or racemic mixture thereof.

In a preferred embodiment, there are disclosed compounds of formula I wherein
A is CN, COOH, $NO_2$, COO($C_1$–$C_6$ alkyl), ($C_1$–$C_6$ alkyl)-$NH_2$ or $CONR_6R_7$;
Q is N;
$R_1$ is hydrogen, NHCH($CH_3$) phenyl or NH($CH_2$)$_3$—O—$CH_2CH_3$;
$R_2$, $R_3$ and $R_4$ are independently hydrogen or $CF_3$; and
$R_6$ and $R_7$ are independently hydrogen, $C_1$–$C_6$ alkyl or a saturated 5 to 7 membered heterocyclic ring containing at least one N atom, and optionally containing 1–2 additional N atoms and 0–1 S or O atom; or
$R_6$ and $R_7$ are taken together with the nitrogen atom to form a saturated 6 membered heterocyclic ring containing at least one N atom, and optionally containing 1–2 additional N atoms and 0–1 S or O atom, said ring optionally substituted by 1–3 groups selected from $C_1$–$C_6$ alkyl, halogen, hydroxy, $CF_3$, $NH_2$ and $NO_2$;
or a pharmaceutically acceptable addition salt and/or hydrate thereof, or where applicable, a geometric or optical isomer or racemic mixture thereof.

Representative species falling within the present invention include the following:

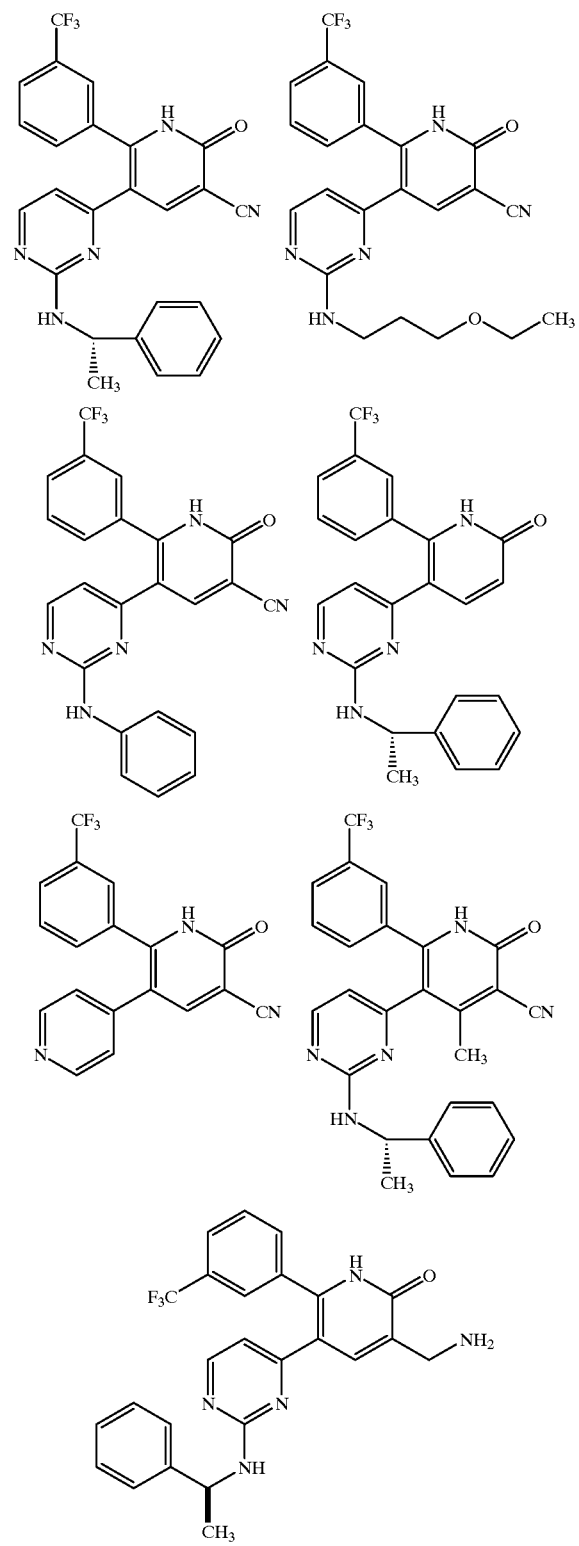

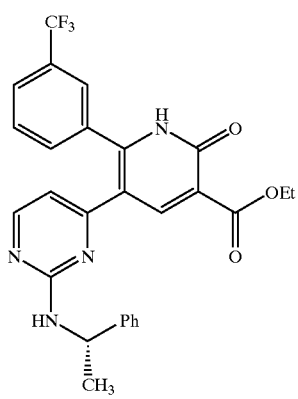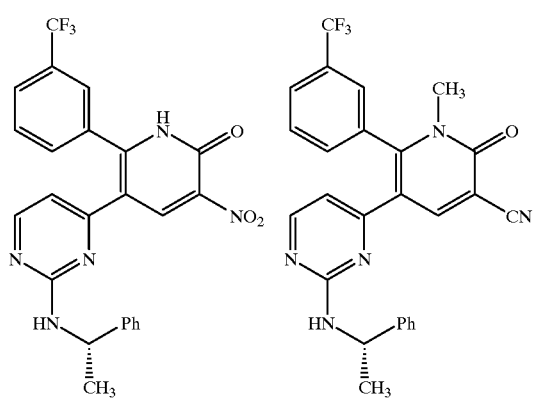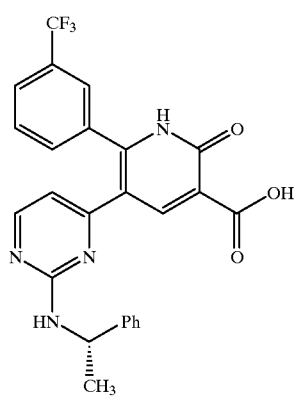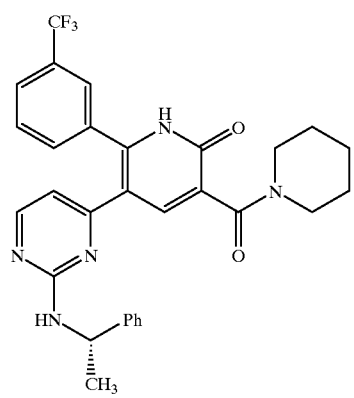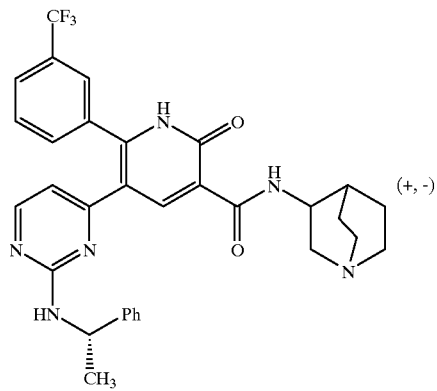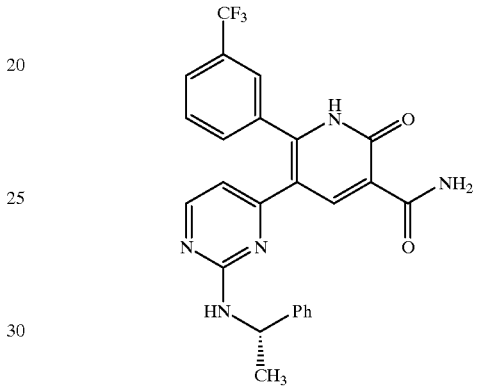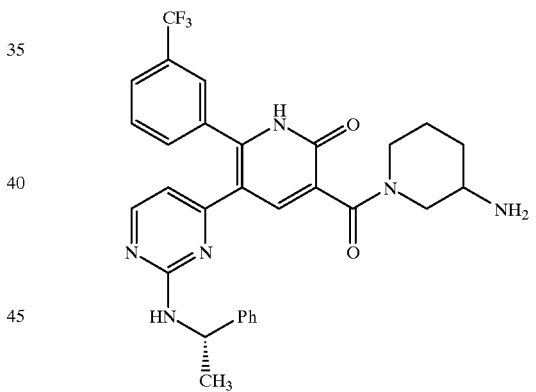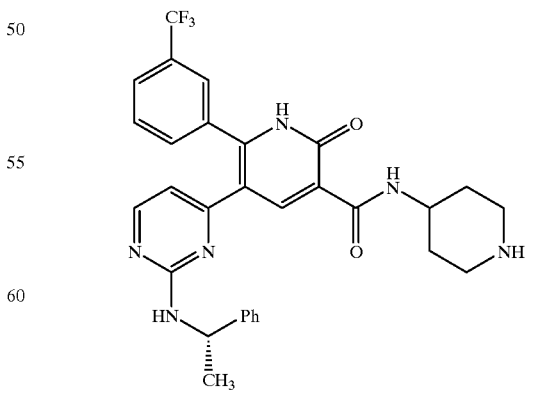

Unless otherwise stated or indicated, the following definitions shall apply throughout the specification and claims.

The term "alkyl" refers to a monovalent alkane (hydrocarbon) derived radical containing from 1 to 15 carbon atoms unless otherwise defined. It may be straight or branched, and when of sufficient size, e.g., $C_{3-15}$ may be cyclic. Preferred straight or branched alkyl groups include methyl, ethyl, propyl, isopropyl, butyl and t-butyl. Preferred cycloalkyl groups include cyclopropyl, cyclopentyl and cyclohexyl.

Alkyl also includes an alkyl group substituted with a cycloalkyl group, such as cyclopropylmethyl.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "aryl" refers to aromatic rings, e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl or naphthyl substituted with one or two groups.

The terms "heterocycloalkyl" and "heterocyclyl" refer to a cycloalkyl group (nonaromatic) in which one of the carbon atoms in the ring is replaced by a heteroatom selected from O, S(O)y or N, and in which up to three additional carbon atoms may be replaced by said heteroatoms. When three heteroatoms are present in the heterocycle, they are not all linked together.

Examples of heterocyclyls are piperidinyl, morpholinyl, azetidinyl, pyrrolidinyl, tetrahydrofuranyl, imidazolinyl, piperazinyl, pyrolidin-2-one, piperidin-2-one and the like.

The term "halogen" or "halo" is intended to include fluorine, chlorine, bromine and iodine.

As used herein, the term "composition" is intended to encompass a product comprising the specified ingredients in the specified amounts, as well as any product which results, directly or indirectly, from combination of the specified ingredients in the specified amounts.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "TNF mediated disease or disease state" refers to disease states in which TNF plays a role, either by production or increased activity levels of TNF itself, or by causing another monokine to be released, such as but not limited to IL-1 or IL6. A disease state in which IL-1, for instance is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

By the term "cytokine interfering or cytokine suppressive amount" is meant an effective amount of a compound of formula I which will cause a decrease in the it vivo activity or level of the cytokine to normal or sub-normal levels, when given to the patient for the prophylaxis or therapeutic treatment of a disease state which is exacerbated by, or caused by, excessive or unregulated cytokine production or activity.

The compounds of the invention are prepared by the following reaction schemes. All substituents are as defined above unless indicated otherwise desired ring substituents to provide ketone 2. Reaction of 2 with a dimethylformamide dialkyl acetal may then be performed by refluxing in a non protic solvent such as toluene to provide enamine 3. Condensation of 3 with nitroacetamide or cyanoacetamide using a metal alkoxide/alcohol as base, affords the pyridone 4.

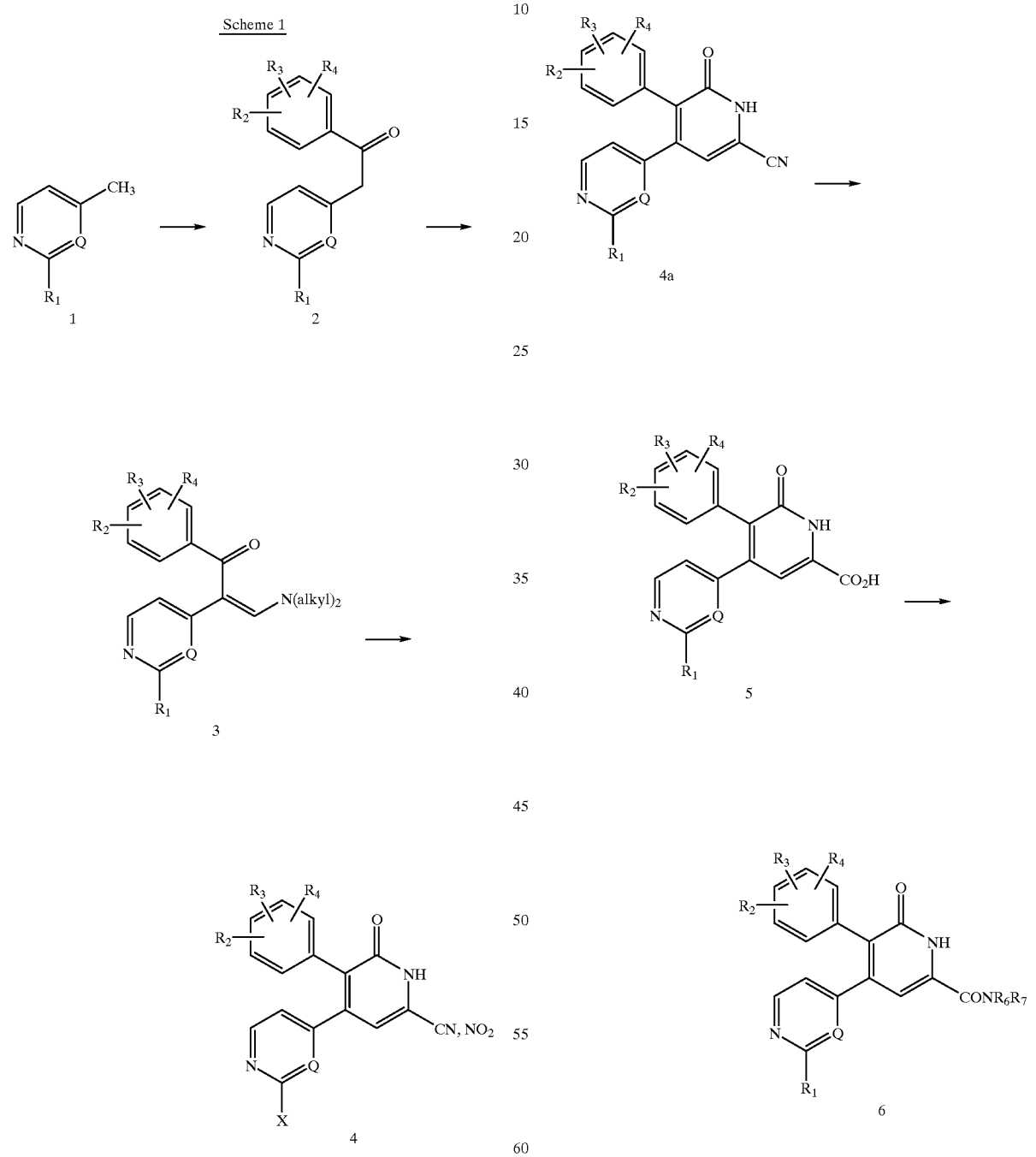

The methyl group of a heterocycle of general structure 1, e.g., 4-methylpyridine, 2-fluoro-4-methylpyridine or 4-methyl-2-methylthiopyrimidine, can be deprotonated with an appropriate base such as an alkyllithium or metal amide and the resulting anion quenched with the N,O-dimethylamide of an aromatic carboxylic acid containing the Nitrile 4a can subsequently be hydrolyzed under either acid or base conditions to give the corresponding acid 5. Coupling with amines $R_6R_7H$ can then be accomplished using one of many coupling agents such as dicyclohexylcarbodiimide to afford amide 6.

Scheme 3

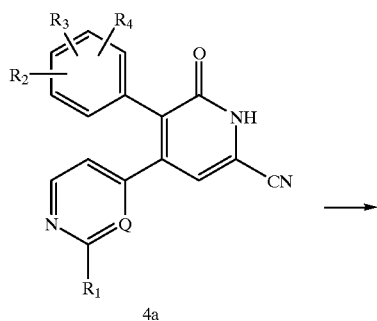
4a

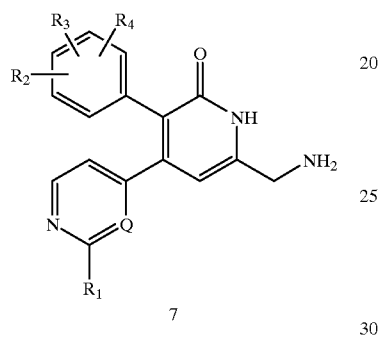
7

Nitrile 4a may also be reduced to the amine 7 either by catalytic reduction or by treatment with cobalt chloride and sodium borohydride in an alcohol solvent.

Scheme 4

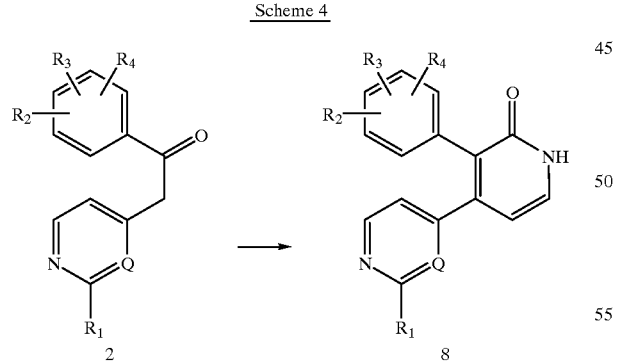

The ketone of formula 2 may also be reacted with an alkyl propiolate and ammonia in an alcohol solvent to provide the pyridone 8.

Scheme 5

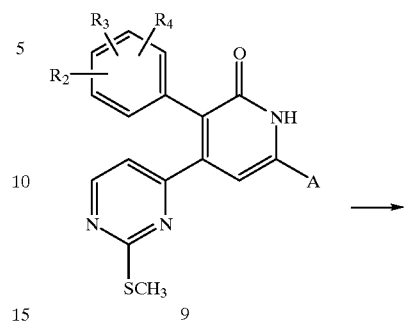
9

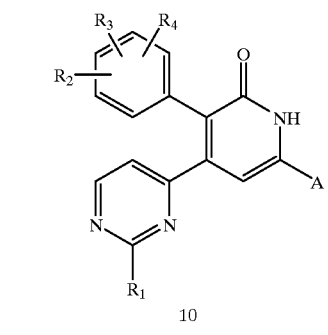
10

A pyridone in which the heterocyclic ring is 2-methylthio-4-pyrimidine 9 can be converted to amine 10 by a two step process. First oxidation to the corresponding sulfone using m-chloroperbenzoic acid or Oxone is followed by reaction with an amine either neat or in an organic solvent.

Scheme 6

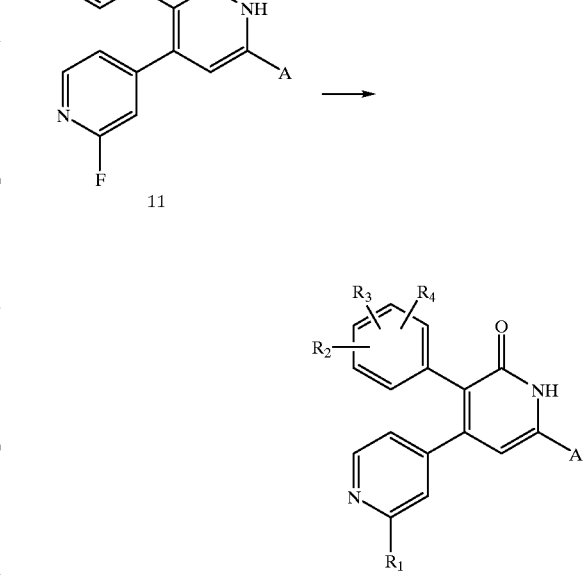

Alternatively, a 2-fluoropyridine 11 can be converted to anamino compound 12 by treatment with an amine at elevated temperature.

The compounds of formula I can be used in the prophylactic or therapeutic treatment of disease states in mammals which are exacerbated or caused by excessive or unregulated cytokines, e.g., IL-1, IL-6, IL-8 or TNF.

Because the compounds of formula I inhibit cytokines, the compounds are useful for treating diseases in which cytokine presence or activity is implicated, such as rheumatoid arthritis, rheumatoid spondylitis, osteoarthritis, gouty arthritis and other arthritic conditions.

The compounds of formula I are useful to treat disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (ADS), AIDS, ARC (AIDS related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds of formula I are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulo-nephritis, in a mammal in need of such treatment, which comprises administering to said mammal a compound of formula I in an amount which is effective for treating said disease or condition.

When administered to a patient for the treatment of a disease in which a cytokine or cytokines are implicated, the dosage used can be varied within wide limits, depending upon the type of disease, the age and general condition of the patient, the particular compound administered, the presence or level of toxicity or adverse effects experienced with the drug and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid, and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxy-ethylene derivatives thereof. Suspending agents such as natural gums, cellulose derivatives or inorganic materials such as silicas, and other ingredients such as lanolin may also be included.

The following examples illustrate the preparation of some of the compounds of the invention and are not to be construed as limiting the scope of the invention disclosed herein.

EXAMPLE 1

2-Oxo-5-[2-((S)-1-phenylethylamino)-pyrimidin-4-yl]-6-(3-trifluoromethylphenyl)-1,2-dihydropyridine-3-carbonitrile

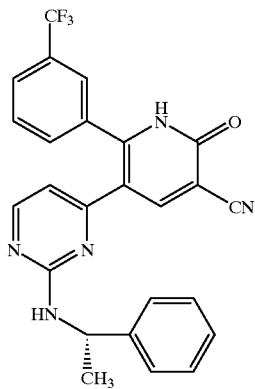

Step 1A: 2-Methylthio-4-methylpyrimidine

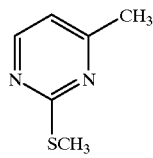

To 2-mercapto-4-methylpyrimidine.HCl(50.0 g, 0.307mole) in toluene (750 mL) under argon, was added diisopropylethylamine (80.0 mL, 0.461 mole) followed by N,N-dimethylformamide dimethyl acetal (100 mL) and the mixture heated to reflux for 4 hours. Upon cooling the reaction was concentrated in vacuo to an oil, dissolved in ether (400 mL), and washed with water (2×50 mL). The organic extract was dried over sodium sulfate, filtered and concentrated to an oil which was vacuum distilled to give 2-methylthio-4-methylpyrimidine (36.4 g, 84%) as an oil.

$^1$H NMR(CDCl3) d 8.37 (d, 1H, J=7.5Hz), 6.82 (d, 1H, J=7.5Hz), 2.55 (S, 3H), 2.45 (S, 3H).

Step 1B: 2-(2-Methylthio-pyrimidin-5-yl)-1-(3-trifluoromethylphenyl)-ethanone

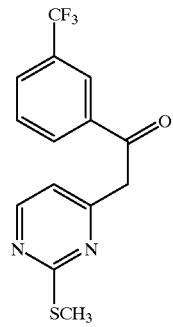

To a solution of diisopropylamine (7.9 mL, 0.056 mole) in THF (100 mL) at −78° C. and under argon was added 2.5M n-butyllithium (22.5 mL, 0.056 mole) followed, after 5 minutes, by a solution of 2-methylthio-4-methylpyrimidine (5.27 g, 0.376 mole) in THF (20 mL). Upon stirring for 15 min. at −78° C., a solution of N-methoxy-N-methyl-3-trifluoromethylbenzamide (9.63 g, 0.041 mole) in THF (90 mL) was added. The reaction was allowed to warm to 0° C. and then quenched into water (400 mL) and ethyl acetate (400 mL). The layers were separated and the aqueous layer washed with ethyl acetate (200 mL). The ethyl acetate extracts were combined, dried over anhydrous sodium sulfate, filtered, and concentrated to a solid (11.9 g). Trituration from 10% ether/hexane (100 mL) gave 9.5 g (78%) of the title compound.

$^1$H NMR (CDCl3) d 6.6–8.5 (m, 6H, rotamers), 2.62 (S, 3H), 1.58 (S, 3H).

Step 1C: Dimethylamino-2-(2-methylsulfanylpyrimidin-4-yl)-1-(3-trifluoromethylphenyl)-prop-2-en-1-one

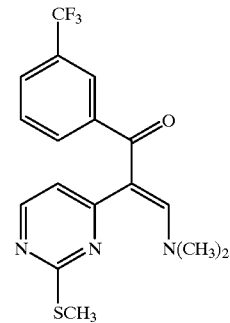

To a mixture of 2-(2-methylthio-pyrimidin-5-yl)-1-(3-trifluoromethylphenyl)-ethanone (5.0 g, 0.0160 mole) in toluene (40 mL) was added dimethylformamide dimethylacetal (4.0 mL, 0.033 mole) and the mixture stirred at reflux for 5 hours. Additional DMF dimethyl-acetal was added (4.0 mL, 0.033 mole) and the mixture allowed to stir at reflux for 18 hrs. The reaction was cooled and concentrated in vacuo to give 5.88 gms (100%) of the title compound as an oil.

MS (FAB)—M$^{+1}$368

Step 1D: 5-(2-methylsulfanylpyrimidin-4-yl)-2-oxo-6-(3-trifluoromethylphenyl)-1,2-dihydropyridine-3-carbonitrile

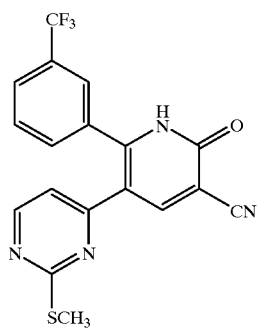

To a mixture of cyanoacetamide (1.42 gm, 0.0169 mole) in ethanol (20 mL) was added a solution of sodium ethoxide (6.3 mL, 21 wt % solution, 0.0169 mole) in ethanol. The mixture was stirred for 5 minutes and dimethylamino-2-(2-methylsulfanylpyrimidin-4-yl)-1-(3-trifluoromethyl-phenyl)-prop-2-en-1-one (5.88 gm, 0.0160 mole) in ethanol (40 mL) added. The reaction was stirred for 18 hrs at room temperature and then concentrated to an oil. The oil was dissolved in ethyl acetate (50 mL) and water (50 mL) and the pH adjusted to 5.0 with a 10% solution of sodium hydrogen sulfate. The ethyl acetate layer was removed, dried over sodium sulfate, and concentrated to an oil. The oil was chromatographed on silica eluting with 5% acetone/dichloromethane to give 4.0 gm (68%) of the title compound as an oil.

NMR (300 MHz, CD$_3$OD) δ: 8.53(s, 1H), 8.35(d, 1H), 7.84(d, 1H), 7.74 (s, 1H), 7.58–7.7(m, 2H), 6.85(d, 1H), 2.19(s, 3H).

Step 1E: 5-(2-methylsulfonylpyrimidin-4-yl)-2-oxo-6-(3-trifluoromethylphenyl)-1.2-dihydropyridine-3-carbonitrile

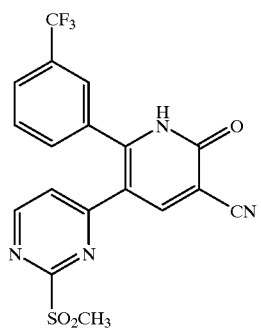

To a solution of 5-(2-methylsulfanylpyrimidin-4-yl)-2-oxo-6-(3-trifluoromethylphenyl)-1,2-dihydropyridine-3-carbonitrile (0.40 gm, 0.00104 mole) in methanol (40 mL) was slowly added a solution of Oxone (1.90 gm, 0.0030 mole) in water (40 mL). The mixture was allowed to stir for 30 minutes and then acetone (20 mL) added. The reaction was then stirred for 48 hrs, and then concentrated to remove the acetone and methanol. The resulting mixture was dis-solved in ethyl acetate and water and the pH adjusted to 7.0 with 10% aqueous sodium hydrogen sulfate. The ethyl acetate layer was removed and aqueous layer washed with ethyl acetate. The ethyl acetate extracts were dried over sodium sulfate and concentrated to give 0.25 gm (57%) of the title compound.

NMR (300 MHz, CD$_3$OD) δ: 8.68(d, 1H), 8.47(s, 1H), 7.74(m, 2H), 7.56(m, 2H), 7.32(d, 1H), 3.04(s, 3H).

Step 1F: 2-Oxo-5-[2-(1-phenylethylamino)-pyrimidin-4-yl]-6-(3-trifluoromethylphenyl)-1,2-dihydropyridine-3-carbonitrile To 5-(2-methylsulfonylpyrimidin-4-yl)-2-oxo-6-(3-trifluoromethylphenyl)-1,2-dihydropyridine-3-carbonitrile (150 mg, 0.357 mmol) in a sealed tube was added (S)-methylbenzylamine (150 mg) and the mixture heated under argon at 100° C. for 1 hour. The reaction was cooled and the oil dissolved in ethyl acetate (25 mL). The solution was washed 3 times with a pH 5.3 buffer solution of 10% citric acid/NaOH (15 mL). The ethyl acetate layer was dried over sodium sulfate concentrated and chromatographed on silica using 80% ethyl acetate/hexane to give 120 mg (73%) of the title compound as a solid. The solid was stirred in methanol/hexane (2 mL) for 1 hour, filtered, and dried 40° C. to give 105 mg of a solid.

MS (FAB)—M$^{+1}$=462

Analysis Calcd. for C$_{25}$H$_{18}$F$_3$N$_5$O: C, 65.07; H, 3.93; N, 15.18; Found: C, 64.99; H, 4.00; N, 15.24.

EXAMPLE 2

2-Oxo-5-[2-(3-ethoxypropylamino)-pyrimidin-4-yl]-6-(3-trifluoromethylphenyl)-1.2-dihydropyridine-3-carbonitrile

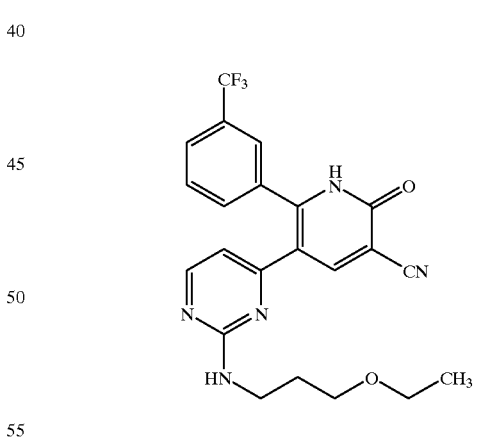

The title compound was prepared in a similar manner to that described in Example 1, step F using 3-ethoxypropylamine in place of (S)-α-methylbenzylamine. Purification of the product by preparative HPLC (C-18, CH$_3$CN/water with 0.1% trifluoroacetic acid) gave the trifluoroacetic acid salt upon lyophilization.

MS (FAB)—M$^{+1}$=444

EXAMPLE 3

2-Oxo-5-[2-(phenylamino)-pyrimidin-4-yl]-6-(3-trifluoromethylphenyl)-1,2-dihydropyridine-3-carbonitrile

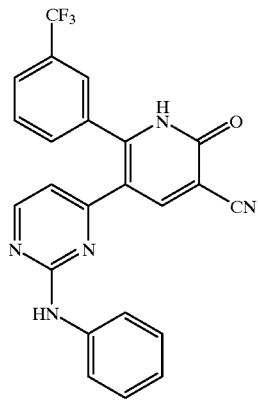

To 5-(2-methylsulfonylpyrimidin-4-yl)-2-oxo-6-(3-trifluoromethylphenyl)-1,2-dihydropyridine-3-carbonitrile (160 mg, 0.35 mmol) in DMF, under argon, was added a prepared mixture of aniline (129 µL, 1.30 mmole) and potassium bis(trimethylsilyl)amide (0.5M in toluene) (2.6 mL, 1.30 mmole) under argon. The reaction was stirred for 15 minutes and then quenched into ethyl acetate and water. The pH was adjusted to 5.4 with aqueous potassium hydrogen sulfate solution and the ethyl acetate layer removed and concentrated to give a solid. Trituration of the solid from methanol (4 mL) gave 80 mg of a solid.

MS analysis—$M^{+1}$=434.

EXAMPLE 4

(S)-5-(2-(1-Phenyethyl)aminopyrimidin-4-yl)-6-(3-trifluoromethylphenyl)-2-pyridone

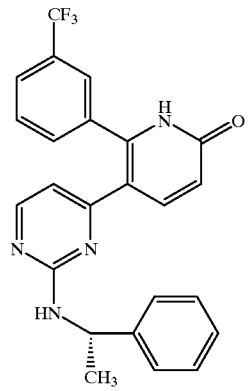

Step 4A: 5-(2-methylsulfanylpyrimidin-4-yl)-2-oxo-6-(3-trifluoromethylphenyl)-1,2-dihydropyridine

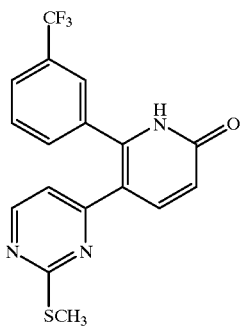

2-(2-Methylthiopyrimidin-5-yl)-1-(3-trifluoromethylphenyl)-ethanone (0.5 gm, 1.60 mmole), methyl propiolate (0.36 mL, 3.2 mmole) and 2.0 M ammonia/methanol (10 mL) were combined in a pressure vessel and heated at 100° C. for 10 hours. The reaction was cooled and concentrated to an oil. Purification of the product by preparative HPLC (C-18 CH₃CN/water with 0.1% trifluoroacetic acid) followed by extraction of the product into methylene chloride from 10% aqueous sodium bicarbonate gave 66 mg (11%) of the title compound upon evaporation.

MS (FAB)—$M^{+1}$=364.

Step 4B: (S)-5-(2-(1-Phenyethyl)aminopyrimidin-4-yl)-6-(3-trifluoromethylphenyl)-2-pyridone The title compound was prepared in an analogous manner to that described in Example 1, Steps E and F using 5-(2-methylsulfanyl-pyrimidin-4-yl)-2-oxo-6-(3-trifluoromethylphenyl)-1,2-dihydropyridine.

MS (FAB)—$M^{+1}$=437.

EXAMPLE 5

2-Oxo-5-(4-pyridyl)-6-(3-trifluoromethylphenyl)-1,2-dihydropyridine-3-carbonitrile

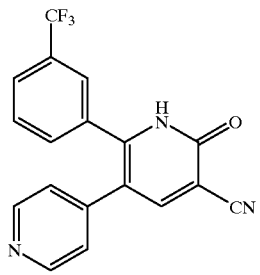

The title compound was prepared in an analogous manner to that described in Example 1, Steps B–D using 4-picoline in place of 2-methylthio-4-methylpyrimidine.

MS (FAB)—$M^{+1}$=342

EXAMPLE 6

2-Oxo4-methyl-5-[(S)-2-(1-phenylethylamino)-pyrimidin-4-yl]-6-(3-trifluoromethylphenyl)-1,2-dihydropyridine-3-carbonitrile

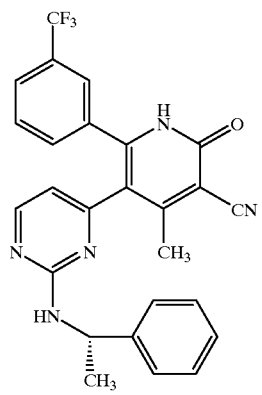

Step 6A: 3-Ethoxy-2-(2-methylsulfanylpyrimidin-4-yl)-1-(3-trifluoromethylphenyl)-but-2-en-1-one To 2-(2-methylthio-pyrimidin-5-yl)-1-(3-trifluoromethylphenyl)-ethanone (1.0 gm, 0.0032 mole) under argon was added triethylorthoacetate (30 mL) and the mixture refluxed for 18 hrs. Removal of solvent by distillation (20 mL) followed by addition of additional triethylorthoacetate (20 mL) and refluxing for another 2 hrs gave complete reaction. The reaction mixture was cooled, concentrated in vacuo to an oil, and dissolved in ethyl acetate (50 mL). The ethyl acetate solution was washed with 10% aqueous sodium bicarbonate (20 mL), dried over sodium sulfate and concentrated to an oil. The oil was chromatographed on silica using 25% ethyl acetate/hexane to give 0.52 gm of a mixture of isomers of the title compound as an oil. The cride oil was used in the next step without further purification.

Step 6B 2-Oxo4-methyl-5-[(S)-2-(1-phenylethylamino)-pyrimidin-4-yl]-6-(3-trifluoromethylphenyl)-1,2-dihydropyridine-3-carbonitrile The title compound was prepared in an analogous manner to that described in Example 1, Steps D–F using 3-ethoxy-2-(2-methylsulfanylpyrimidin-4-yl)-1-(3-trifluoromethylphenyl)-but-2-en-1-one. Purification of the product by preparative chromatography C-18 (CH$_3$CN/water with 0.1% trifluoroacetic acid) gave the trifluoroacetic acid salt upon lyophilization.

MS analysis—M$^{+1}$=476.

NMR (300 MHz, CD$_3$OD) δ: 8.40(d, 1H), 7.70(d, 1H), 7.60(s, 1H), 7.20–7.45(m, 7H), 6.27(d, 1H), 5.05(q, 1H), 2.12(br s, 3H), 1.50(d, 3H).

EXAMPLE 7

3-Aminomethyl-2-oxo-5-[2-((S)-1-phenylethylamino)-pyrimidin-4-yl]-6-(3-trifluoromethylphenyl)-1,2-dihydropyridine

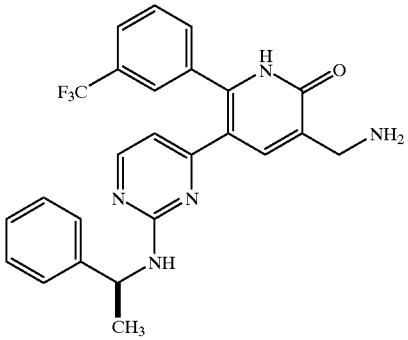

2-Oxo-5-[2-((S)-1-phenylethylamino)-pyrimidin-4-yl]-6-(3-trifluoromethylphenyl)-1,2-dihydropyridine-3-carbonitrile (prepared as described for example 1) (50 mg, 0.11 mmol) was dissolved in warm methanol (1 mL), the solution cooled to ambient temperature then cobalt (II) chloride hexahydrate (52 mg, 0.22 mmol) and sodium, borohydride (41 mg, 1.09 mmol) added in portions. The reaction was stirred 70 minutes then diluted with 5 mL 10% KHSO4 and extracted with ethyl acetate (1×5 mL). The aqueous layer was basified using concentrated ammonium hydroxide then extracted with ethyl acetate (2×5 mL). The combined ethyl acetate extracts were washed with brine, dried over sodium sulfate, filtered, concentrated to to a pale yellow oil. Purification of the product by preparative HPLC (C-18 CH$_3$CN/water with 0.1% trifluoroacetic acid) gave the trifluoroacetic acid salt upon lyophilization.

MS (FAB)—M$^{+1}$=466.1.

NMR (300 MHz, CD$_3$OD) δ: 8.01(d, J=4.9 Hz, 1H), 7.85(bs, 1H), 7.80(d, J=8.0Hz, 1H), 7.65–7.55(m, 3H), 7.29–7.18(m, 6H), 6.19(bs, 1H), 4.04(s, 2H), 1.41(d,J=6.1 Hz, 6H).

EXAMPLE 8

2-Oxo-5-[2-(S)-1-phenylethylamino)pyrimidin-4-yl]-6-(3-trifluoromethylphenyl)-1,2-dihydropyridine-3carboxylic acid ethyl ester

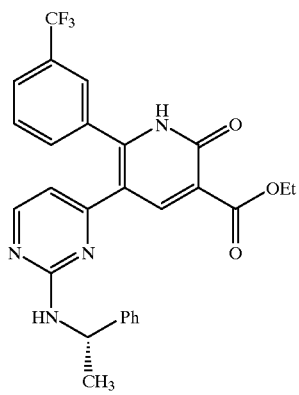

The title compound was prepared in an analogous manner to that described in Example 1, Steps D–F using ethyl malonate monamide in place of cyanoacetamide. Purification of the product of step F by preparative HPLC (C-18 CH₃CN/water with 0.1% trifluoroacetic acid) gave the trifluoroacetic acid salt upon lyophilization as a solid.

NMR (300 MHz, CD₃OD) δ: 8.65 (s, 1H), 8.01 (s, 1H), 7.83–7.78 (m, 2H), 7.67 (m, 2H), 7.32–7.21 (m, 5H), 6.35 (bs, 1H), 4.87 (bs, 1H), 4.40 (q, 2H, 7.1 Hz), 1.47 (d, 3H, 6.9Hz), 1.40 (7, 3H, 7.1 Hz)

EXAMPLE 9

3-Nitro-5-[2-(S-1-phenylethylamino)pyrimidin-4-yl]-6-(3-trifluoromethylphenyl)-1H-pyridine-2-one

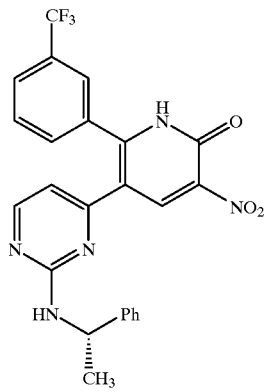

The title compound was prepared in an analogous manner to that described in Example 1, Steps D–F using nitroacetamide in place of cyanoacetamide. Purification of the product of step F by preparative HPLC (C-18 CH₃CN/water with 0.1% trifluoroacetic acid) gave the trifluoroacetic acid salt upon lyophilization as a solid.

NMR (300 MHz, CD₃OD) δ: 8.81 (s, 1H), 8.01 (d, 1H, J=5.6 Hz), 7.87–7.83 (m, 1H), 7.81 (s, 1H), 7.69–7.67 (m, 2H), 7.32–7.29 (m, 4H), 7.24–7.18 (m, 1H), 6.23 (s, 1H), 4.75 (s, 1H), 1.48 (d, 1H, J=6.8 Hz)

EXAMPLE 10

1-Methyl-2-oxo-5-[2-(S-1-phenylethylamino)-pyrimidin-4yl]-6-(3-trifluoromethylphenyl)-1,2,-dihydropyridine-3-carbonitrile

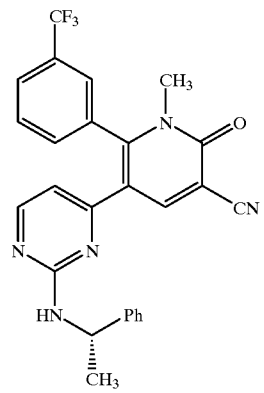

Step 10A: 1-Methyl-5-(2-methylsulfanylpyrimidin-4-yl)-2-oxo-6-(3-trifluoromethylphenyl)-1,2-dihydropyridine-3-carbonitrile

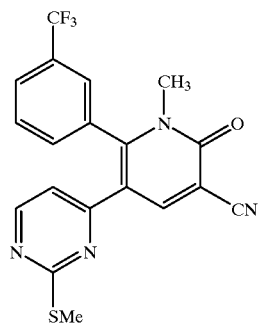

To a solution of 5-(2-methylsulfanylpyrimidin-4-yl)-2-oxo-6-(3-trifluoromethylphenyl)-1,2-dihydropyridine-3-carbonitrile (150 mg, 0.00040 mol) in 3 mL DMF was added cesium carbonate (200 mg, 0.00060 mol) and methyl iodide (1 mL, 0.0154 mol) and the solution stirred at room temperature for 1 h. The mixture was the partitioned between H₂O and EtOAc and the organic phase dried over anhydrous sodium sulfate and concentrated. Chromatography on silica with 3% MeOH in CH₂Cl₂ yields 100 mg (65%) 1-methyl-5-(2-methylsulfanyl-pyrimidin-4-yl)-2-oxo-6-(3-trifluoromethyl-phenyl)-1,2-dihydropyridine-3-carbonitrile as a solid.

Step 10B: 1-Methyl-2-oxo-5-[2-(S-1-phenyl-ethylamino)-pyrimidin- 4-yl]-6-(3-trifluoromethyl-phenyl)-1,2,-dihydropyridine-3-carbonitrile The title compound was prepared in an analogous manner to that described in Example 1, Steps E and F. Purification of the product of step F by preparative HPLC (C-18 CH₃CN/water with 0.1% trifluoroacetic acid) gave the trifluoroacetic acid salt upon lyophilization as a solid.

NMR (300 MHz, CD₃OD) : δ8.10–7.62 (m, 6H), 7.36–7.24 (m, 5H), 6.01 (m, 1H), 4.88 (m, 1H), 3.33 (s, 3H), 1.48 (m, 3H)

EXAMPLE 11

2-Oxo-5-[2-(S-1-phenyl-ethylamino)-pyrimidin-4-yl]-6-(3-trifluoromethyl-1-phenyl)-1,2-dihydro-pyridin-3-carboxylic acid 2-Oxo-5-[2-((S)-1-phenylethylamino)-pyrimidin-4-yl]-6-(3-trifluoromethylphenyl)-1,2-dihydropyridine-3-carbonitrile (2.5 g, 0.00541) was dissolved in 15 mL MeOH and 50 mL 10N NaOH and heated to reflux for 60 h. The reaction was then allowed to cool and acidified with 1N HCl. The resultant precipitate was filtered on a medium frit and the gummy solid sucked to dryness to yield 2.33 g (89%) of a solid.

NMR (300 MHz, CD$_3$OD) : δ8.49 (s, 1H), 8.03 (m, 1H), 7.64–7.45 (m, 4H), 7.32–7.15 (m, 5H), 6.37 (m, 1H), 4.80 (m, 1H), 1.37 (d, 3H) MS (FAB)—M$^{+1}$=481.2

EXAMPLE 12

5-[2-(S-1-Phenylethylamino)-pyrimidin-4-yl]-3-(piperidine-1-carbonyl)-6-(3-trifluoromethylphenyl)-1H-pyridin-2-one

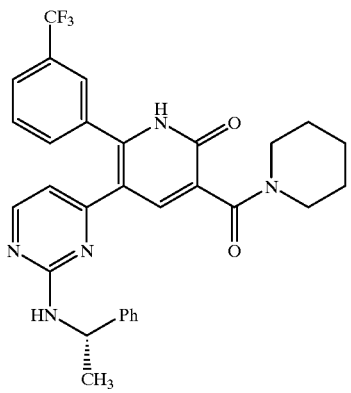

2-Oxo-5-[2-(S-1-phenyl-ethylamino)-pyrimidin-4-yl]-6-(3-trifluoromethyl-1-phenyl)-1,2-dihydro-pyridin-3-carboxylic acid (100 mg, 0.00020 mol) was dissolved in SOCl$_2$ and stirred at rt for 2 h. The reaction was concentrated and azeotroped with toluene (X3) and the residue dissolved in 2 mL CH$_2$Cl$_2$ before adding 50 mg (0.00058 mol) piperidine and monitoring the reaction by HPLC. After 1 h the reaction was concentrated and purified by preparative HPLC (C-18 CH$_3$CN/water with 0.1% trifluoroacetic acid) to yield the trifluoroacetic acid salt after lyophilization.

NMR (300 MHz, CD$_3$OD): δ7.96 (d, 1H, J=5.8 Hz), 7.85–7.80 (m, 3H), 7.69–7.67 (m, 2H), 7.32–7.21 (m, 5H), 6.28 (s, 1H), 4.76 (m, 1H), 3.74 (m, 2H), 3.39 (m, 2H), 1.72–1.61 (m, 6H), 1.48 (d, 3H, J=6.9 Hz)

EXAMPLE 13

2-Oxo-5-[2-(S-1-phenylethylamino)-pyrimidin-4-yl] 1-6-(3-trifluoromethylphenyl)-1,2-dihydro-pyridine-3-carboxylic acid (+,−) (1-azabicyclo[2.2.2] oct-3-yl) amide

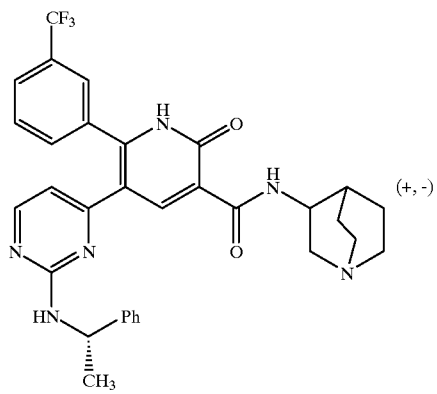

The title compound was prepared in an analogous manner to that described in Example 12 using (+,−) aminoquinucli-dine in place of piperidine. Purification of the product by preparative HPLC (C-18 CH$_3$CN/water with 0.1% trifluoroacetic acid) gave the trifluoroacetic acid salt as a solid.

NMR (300 MHz, CD$_3$OD): δ8.80 (d, 1H, J=5.6 Hz), 7.95–7.84 (m, 3H), 7.68–7.63 (m, 2H), 7.33–7.18 (m, 5H), 6.24 (s, 1H), 4.75–4.51 (m, 2H), 3.92–3.84 (m, 1H), 3.52–3.35 (m, 4H), 2.40–2.05 (m, 5H), 1.28 (m, 3H)

EXAMPLE 14

2-Oxo-5-[2-(S-1-phenylethylamino)-pyrimidin-4-yl]-6-(3-trifluoromethylphenyl)-1,2-dihydro-pyridine-3-carboxylic acid amide

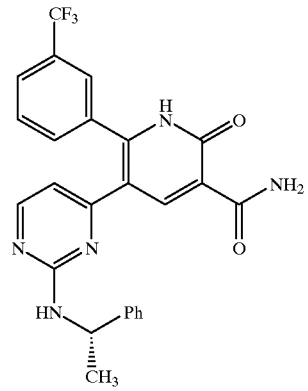

The title compound was prepared in an analogous manner to that described in Example 12 replacing piperidine with a saturated solution of ammonia in dichloromethane. Purification of the product by preparative HPLC (C-18 CH$_3$CN/water with 0.1% trifluoroacetic acid) gave the trifluoroacetic acid salt as a solid.

NMR (300 MHz, CD$_3$OD): δ8.90 (s, 1H), 8.02 (m, 1H), 7.86 (m, 2H), 7.69 (m, 2H), 7.35–7.18 (m, 5H), 6.46 (s, 1H), 4.74 (s, 1H), 1.44 (d, 3H, J=6.8 Hz)

EXAMPLE 15

3-(3-Aminopiperidine-1-carbonyl)-5-[2-(S-1-phenylethylamino)-pyrimidine-4-yl]-6-(3-trifluoromethylphenyl)-1H-pyridin-2-one

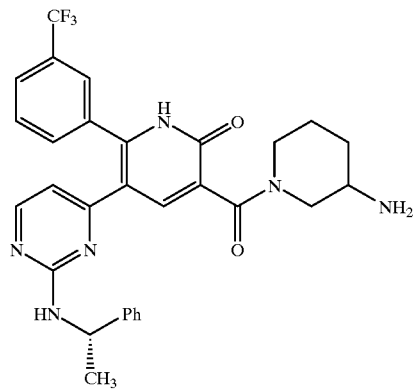

The title compound was prepared in an analogous manner to that described in Example 12 using 3-(t-butoxycarbonylamino)-piperidine in place of piperidine. In a separarte step, the BOC group was removed by stirring the coupled material in 3 mL CH$_2$Cl$_2$ and 2 mL TFA overnight. Concentration and subsequent purification of the product by preparative HPLC (C-18 CH$_3$CN/water with 0.1% trifluoroacetic acid) gave the trifluoroacetic acid salt as a solid.

NMR (300 MHz, CD$_3$OD): δ8.27–7.64 (m, 6H), 7.27–7.19 (m, 5H), 6.23 (m, 1H), 4.76 (m, 1H), 4.23 (m, 1H), 4.00–3.20 (m, 6H), 2.10 (m, 1H), 2.00–1.60 (m, 3H), 1.44 (m, 3H)

EXAMPLE 16

2-Oxo-5-[2-(S-1-phenylethylamino)-pyrimidin-4-yl]-6-(3-trifluoromethylphenyl)-1,2-dihydro-pyridine-3-carboxylic acid piperidine-4-ylamide

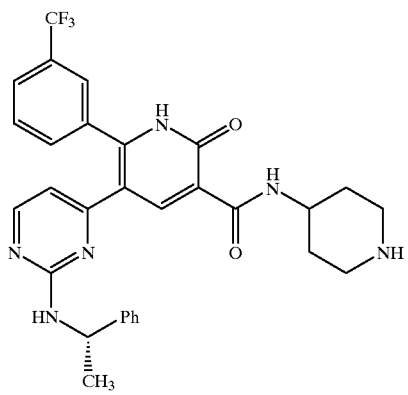

The title compound was prepared in an analogous manner to that described in Example 15 using 4-amino-t-butoxycarbonyl piperidine in place of 3-(t-butoxycarbonylamino)-piperidine.

NMR (300 MHz, CD$_3$OD): δ8.87 (s, 1H), 8.00–7.66 (m, 5H), 7.32–7.18 (m, 5H), 6.36 (s, 1H), 4.71 (m, 1H), 4.20 (m, 1H), 3.48–3.16 (m, 4H), 2.30 (m, 2H), 1.85 (m, 2H), 1.43 (m, 3H)

The ability of compounds of the present invention to inhibit the synthesis or the activity of cytokines can be demonstrated using the following in vitro assays.

BIOLOGICAL ASSAYS

Lipopolysaccharide Mediated Production of Cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 0.6 mL of sodium- heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed two times in Hanks Balanced Salt Solution and then resuspended to a final concentration of 2×10$^6$ cell/mL in RPMI containing 5% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 hours at 37° C. in 5% CO$_2$. At the end of the culture period, cell culture supernatants are assayed for IL-1β, TNF-α, IL-6 and PGE2 production using specific ELISA.

IL-1 MEDIATED CYTOKINE PRODUCTION

Human peripheral blood mononuclear cells are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium- heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of 2×10$^6$ cell/mL in RPMI containing 10% fresh autologous human serum, penicillin streptomycin (10 U/mL) and 0.05% DMSO. Endotoxin free recombinant human IL-1 β is then added to a final concentration of 50 pMolar. An aliquot (0.1 mL) of the cells is quickly dispensed into each well of a 96 well plate containing 0.1 mL of the compound at the appropriate dilution, and are incubated for 24 hours. at 37° C. in 5% CO2. At the end of the culture period, cell culture supernatants are assayed for TNF-α, IL-6 and PGE2 synthesis using specific ELISA.

Determination of IL-1β, TNF-α, IL-6 and Prostanoid Production from LPS or IL-1 Stimulated PBMC's

IL-1β ELISA

Human IL-1β can be detected in cell-culture supernatants or whole blood with the following specific trapping ELISA. Ninety-six well plastic plates (Immulon 4; Dynatech) are coated for 12 hours at 4° C. with 1 mg/mL protein-A affinity chromatography purified mouse anti-human IL-1β monoclonal antibody (purchased as an ascites preparation from LAO Enterprise, Gaithersburg Mad.) diluted in Dulbecco's phosphate-buffered saline (—MgCl$_2$, —CaCl$_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1β standards are prepared from purified recombinant IL-1β produced from *E. coli*. The highest concentration begins at 10 ng/mL followed by 11 two-fold serial dilutions. For detection of IL-1β from cell culture supernatants or blood plasma, 10–25 mL of supernatant is added to each test well with 75–90 mL of PBS Tween. Samples arc incubated at room temperature for 2 hours then washed 6 times with PBS Tween on an automated plate washer (Dennly). Rabbit anti-human IL1β polyclonal antisera diluted 1:500 in PBS-Tween is added to the plate and incubated for 1 hour at room temperature followed by six washes with PBS-Tween. Detection of bound rabbit anti-IL-1β IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-α ELISA

Immulon 4 (Dynatech) 96-well plastic plates are coated with a 0.5 mg/mL solution of mouse anti-human TNF-α monoclonal antibody. The secondary antibody is a 1:2500 dilution of a rabbit anti-human TNF-α polyclonal serum purchased from Genzyme. All other operations are identical to those described above for IL-1β. The standards are prepared in PBS-Tween+10% FBS or HS. Eleven 2 fold dilutions are made beginning at 20 ng/mL TNF-α.

IL-6 ELISA

Levels of secreted human IL-6 are also determined by specific trapping ELISA as described previously in Chin and Kostura, *J. Immunol* 151, 5574–5585 (1993). (Dynatech) ELISA plates are coated with mouse anti-human IL-6 monoclonal antibody diluted to 0.5 mg/mL in PBS. The secondary antibody, a rabbit anti-human IL6 polyclonal antiserum, is diluted 1:5000 with PBS-Tween. All other operations are identical to those described above for IL-1b. The standards are prepared in PBS-Tween+10% FBS or HS. Eleven 2 fold dilutions are made beginning at 50 ng/mL IL-6.

PGE$_2$ production

Prostaglandin E2 is detected in cell culture supernatants from LPS or IL-1 stimulated PBMC's using a commercially available enzyme immunoassay. The assay purchased from the Cayman Chemical (Catalogue number 514010) and is run according to the manufacturer's instructions.

Interleukin8 (IL-8)

The present compounds can also be assayed for IL-8 inhibitory activity as discussed below. Primary human umbilical cord endothelial cells (HUVEC) (Cell Systems, Kirkland, Wa.) are maintained in culture medium supplemented with 15% fetal bovine serum and 1% CS-HBGF consisting of aFGF and heparin. The cells are then diluted 20-fold before being plated (250 μl) into gelatin coated 96-well plates. Prior to use, culture medium is replaced with fresh medium (200 μl). Buffer or test compound (25 μl, at appropriate concentrations) is then added to each well in quadruplicate wells and the plates incubated for 6 h in a humidified incubator at 37° C. in an atmosphere of 5% CO$_2$. At the end of the incubation period, supernatant is removed and assayed for IL-8 concentration using an IL-8 ELISA kit obtained from R&D Systems (Minneapolis, Minn.). All data is presented as mean value (ng/mL) of multiple samples based on the standard curve. IC50 values where appropriate are generated by non-linear regression analysis.

What is claimed is:

1. A compound of the formula

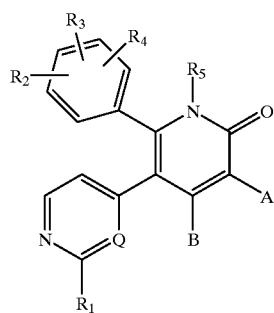

(I)

wherein:

A is CN, COOH, NO$_2$, COO(C$_1$–C$_6$ alkyl), (C$_1$–C$_6$ alkyl)-NH$_2$ or CONR$_6$R$_7$;

Q is N;

R$_1$ is hydrogen, NHCH(CH$_3$)phenyl or NH(CH$_2$)$_3$—O—CH$_2$CH$_3$;

R$_2$, R$_3$ and R$_4$ are independently hydrogen or CF$_3$; and

R$_6$ and R$_7$ are independently hydrogen, C$_1$–C$_6$ alkyl or a saturated 5 to 7 membered heterocyclic ring containing at least one N atom, and optionally containing 1–2 additional N atoms and 0–1 S or O atom; or R$_6$ and R$_7$ are taken together with the nitrogen atom to form a saturated 6 membered heterocyclic ring containing at least one N atom, and optionally containing 1–2 additional N atoms and 0–1 S or O atom, said ring optionally substituted by 1–3 groups selected from C$_1$–C$_6$ alkyl, halogen, hydroxy, CF$_3$, NH$_2$ and NO$_2$;

or a pharmaceutically acceptable addition salt and/or hydrate thereof, or where applicable, a geometric or optical isomer or racemic mixture thereof.

2. A compound represented by one of the following structural formula

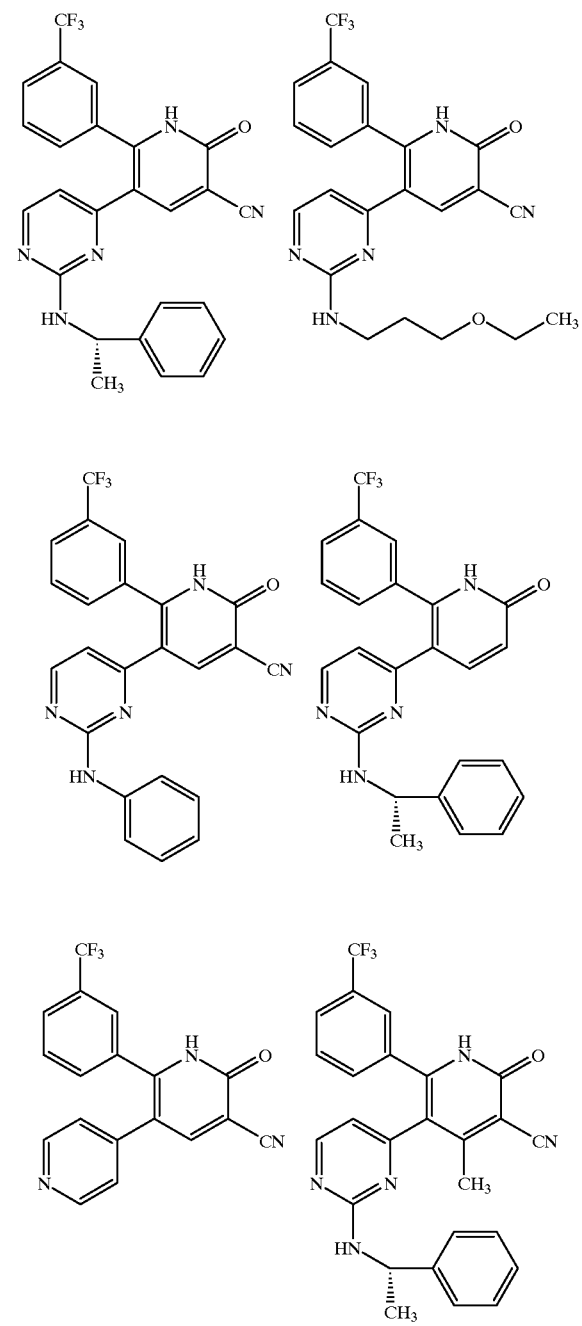

31
-continued
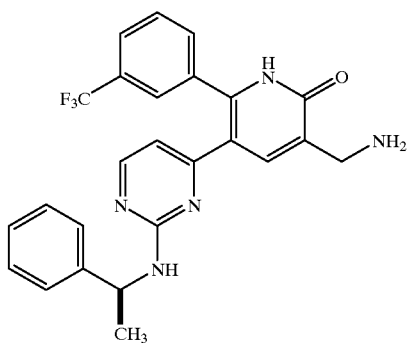
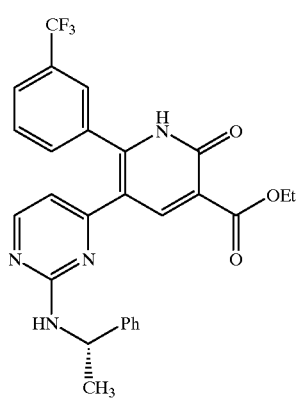
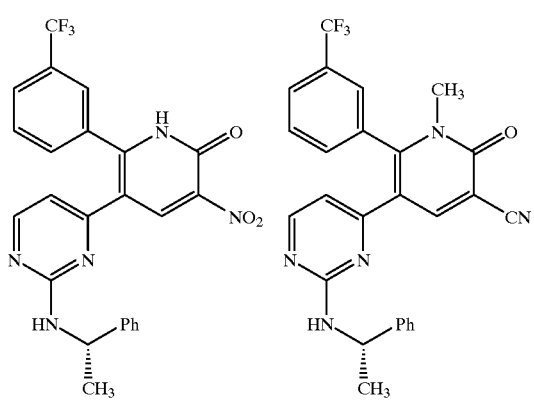
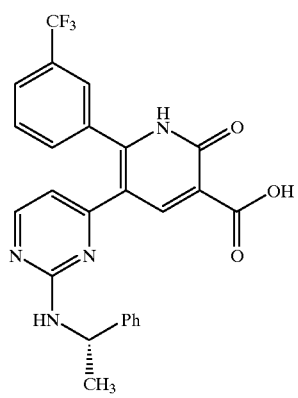
32
-continued
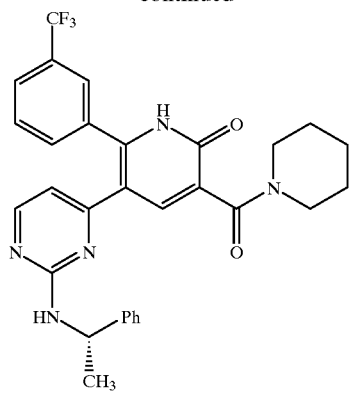
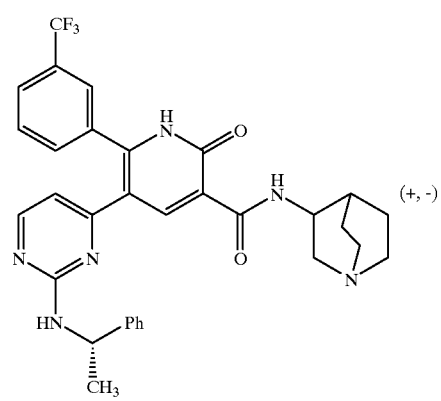
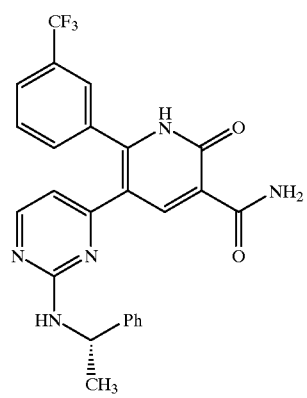
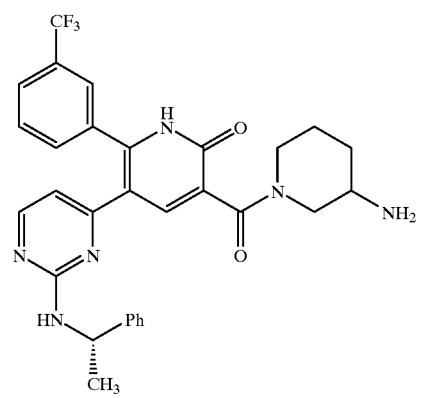

-continued

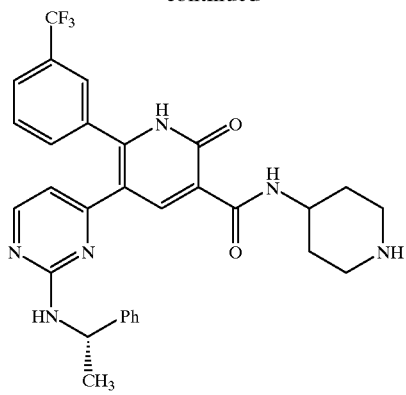

3. A method of treating osteoporosis in a mammalian patient in need of such treatment, which is comprised of administering to said patient an amount of a compound as described in claim 1 which is effective to treat osteoporosis.

4. A method of treating bone resorption in a mammalian patient in need of such treatment, which is comprised of administering to said patient an amount of a compound as described in claim 1 which is effective to treat bone resorption.

* * * * *